US007288500B2

(12) United States Patent
Liu et al.

(10) Patent No.: US 7,288,500 B2
(45) Date of Patent: Oct. 30, 2007

(54) SELECTIVE HYDROGENATION OF NITRO GROUPS OF HALONITRO AROMATIC COMPOUNDS

(75) Inventors: Changkun Liu, Lawrenceville, NJ (US); Bing Zhou, Cranbury, NJ (US)

(73) Assignee: Headwaters Technology Innovation, LLC, Lawrenceville, NJ (US)

( * ) Notice: Subject to any disclaimer, the term of this patent is extended or adjusted under 35 U.S.C. 154(b) by 156 days.

(21) Appl. No.: 11/216,407

(22) Filed: Aug. 31, 2005

(65) Prior Publication Data
US 2007/0049772 A1  Mar. 1, 2007

(51) Int. Cl.
B01J 31/00 (2006.01)
C07C 209/00 (2006.01)

(52) U.S. Cl. .................. 502/155; 502/171; 502/406; 564/422

(58) Field of Classification Search ............ 502/151, 502/171, 406; 564/422
See application file for complete search history.

(56) References Cited

U.S. PATENT DOCUMENTS

| | | |
|---|---|---|
| 3,992,331 A | 11/1976 | Petrow et al. |
| 4,070,401 A | 1/1978 | Hirai et al. |
| 4,148,750 A | 4/1979 | Pine |
| 4,336,240 A | 6/1982 | Moseley et al. |
| 4,347,232 A | 8/1982 | Michaelson |
| 4,366,085 A | 12/1982 | Ikegami et al. |
| 4,513,098 A | 4/1985 | Tsao |
| 4,581,344 A | 4/1986 | Ledoux et al. |
| 4,760,187 A | 7/1988 | Kosak |
| 4,832,938 A | 5/1989 | Gosser et al. |
| 5,061,671 A | 10/1991 | Kitson et al. |
| 5,128,114 A | 7/1992 | Schwartz |
| 5,132,099 A | 7/1992 | Hiramatsu et al. |
| 5,235,106 A | 8/1993 | Didillon et al. |
| 5,338,531 A | 8/1994 | Chuang et al. |
| 5,352,645 A | 10/1994 | Schwartz |
| 5,372,981 A | 12/1994 | Witherspoon |
| 5,480,629 A | 1/1996 | Thompson et al. |
| 5,496,532 A | 3/1996 | Monzen et al. |
| 5,580,839 A | 12/1996 | Huffman et al. |
| 5,608,112 A | 3/1997 | Schwartz |
| 5,641,723 A | 6/1997 | Bonnemann et al. |
| 5,679,858 A | 10/1997 | Langer et al. |
| 5,846,895 A | 12/1998 | Gila et al. |
| 5,846,898 A | 12/1998 | Chuang et al. |
| 5,859,265 A | 1/1999 | Muller et al. |
| 5,900,386 A | 5/1999 | Freund et al. |
| 5,925,588 A | 7/1999 | Chuang et al. |
| 5,939,220 A | 8/1999 | Gunner et al. |
| 5,961,948 A | 10/1999 | Wanngard |
| 5,962,365 A | 10/1999 | Langer et al. |
| 5,962,741 A | 10/1999 | Baumeister et al. |
| 5,972,305 A | 10/1999 | Park et al. |
| 6,054,507 A | 4/2000 | Funaki et al. |
| 6,090,858 A | 7/2000 | El-Sayed |
| 6,168,775 B1 | 1/2001 | Zhou et al. |
| 6,239,054 B1 | 5/2001 | Shukis et al. |
| 6,294,696 B1 | 9/2001 | Didillon et al. |
| 6,316,673 B2 | 11/2001 | Giera et al. |
| 6,528,683 B1 | 3/2003 | Heidemann et al. |
| 6,551,960 B1 | 4/2003 | Laine et al. |
| 6,676,919 B1 | 1/2004 | Fischer et al. |
| 6,740,615 B2 | 5/2004 | Zhou |
| 6,746,597 B2 | 6/2004 | Zhou et al. |
| 6,815,391 B2 | 11/2004 | Xing et al. |
| 6,908,873 B2 | 6/2005 | Zhou et al. |
| 2003/0104936 A1 | 6/2003 | Mao et al. |
| 2004/0037770 A1 | 2/2004 | Fischer et al. |
| 2004/0087441 A1 | 5/2004 | Bock et al. |
| 2004/0101718 A1 | 5/2004 | Cao et al. |
| 2004/0241502 A1 | 12/2004 | Chung et al. |

FOREIGN PATENT DOCUMENTS

| | | |
|---|---|---|
| EP | 0864362 | 9/1998 |
| GB | 1056125 | 1/1967 |
| JP | 10330103 | 12/1998 |

OTHER PUBLICATIONS

Chemical Abstracts, abstract No. 117:199245 (1992).*
Ahmadi, et al., "Shape-Controlled Synthesis of Colloidal Platinum Nanoparticles" *Science*, vol. 272, pp. 1924-1926 (Jun. 28, 1996).
Lordi, et al., "Method for Supporting Platinum on Single-Walled Carbon Nanotubes for a Selective hydrogenation Catalyst", *Chem. Mater.*, vol. 13, pp. 733-737 (Feb. 10, 2001).

* cited by examiner

*Primary Examiner*—Porfirio Nazario-Gonzalez
(74) *Attorney, Agent, or Firm*—Workman Nydegger

(57) ABSTRACT

A supported catalyst for hydrogenating nitro groups of halonitro compounds manufactured from a support, a solvent, and a plurality of organometallic complexes. The organometallic complexes have the formula:

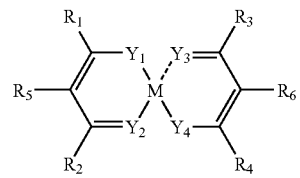

wherein, $R_1$-$R_6$, are independently an R, OR, OC(=O)R, halogen, or combination thereof, where R stands for an alkyl or aryl group; $Y_1$-$Y_4$ are independently an O, S, N, or P atom; and M is a metal atom. The supported catalysts show much higher selectivity and activity when used to hydrogenate nitro groups on halonitro aromatic compounds than catalyst currently being used for such hydrogenation.

21 Claims, No Drawings

SELECTIVE HYDROGENATION OF NITRO GROUPS OF HALONITRO AROMATIC COMPOUNDS

BACKGROUND OF THE INVENTION

1. The Field of the Invention

The present invention relates to catalysts and methods for selective hydrogenation of nitro groups of halonitro aromatic compounds.

2. The Relevant Technology

Aromatic amines are important intermediates in the manufacture of dyes, drugs, herbicides and pesticides. It is known that halonitro aromatic compounds may be reduced to amino aromatic compounds in good yields in the presence of noble metal catalysts and hydrogen (i.e., in a hydrogenation process).

Substantial efforts have been exerted to find conditions in which nitro groups are hydrogenated to form amines without producing undesired side reactions. However, traditional processes for hydrogenating nitro groups often yield undesirable side reactions. For instance, nitro compounds have the tendency to form azo compounds during hydrogenation. For example, the hydrogenation of 2-halo-nitrobenzene can result in formation of substantial amounts of

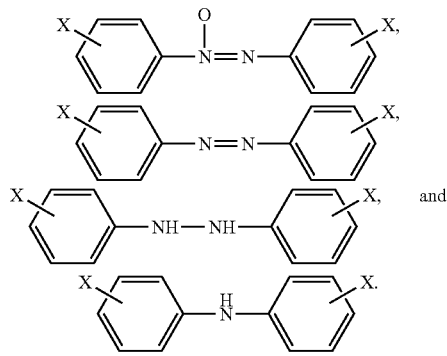

These and other byproducts are often harmful to the environment and are typically expensive to dispose of.

Many important nitro aromatic compounds also include other hydrogenatable groups such as halogens. Dehalogenation has been found to occur when using catalysts made from palladium, platinum, rhodium, nickel and copper chromite. The halogen or other hydrogenatable group is often an important substituent for subsequent reactions or for the final product. Thus, dehalogenation of halonitro aromatic compounds often produces unwanted byproducts. To avoid these undesired byproducts, the nitro group needs to be selectively hydrogenated.

Selective hydrogenation reactions are influenced by many factors. Traditional hydrogenation processes have focused on optimizing conditions by adding catalytic activators, adjusting reaction temperature, adjusting reaction pressure, solvent agitation, and/or modifying other conditions.

BRIEF SUMMARY OF THE INVENTION

The present invention provides various supported catalysts comprised of organometallic compounds dispersed on a solid support. The supported catalysts show much higher selectivity and activity when used to hydrogenate nitro groups on halonitro aromatic compounds compared to catalysts currently used for such hydrogenation reactions.

Supported catalysts according to the invention include a metal center that is coordinated with an acetylacetonate backbone ligand structure. The organometallic complexes have a structure according the following formula:

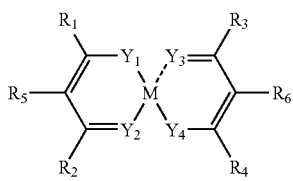

wherein, $R_1$-$R_6$ comprise, independent of one another, one or more of an R, OR, OC(=O)R, or halide, wherein R stands for an alkyl, an aryl, or a hydrogen;

$Y_1$-$Y_4$ are independently an O, S, N, or P atom; and

M is a metal atom.

In a preferred embodiment, the metal atom is selected from the group comprising palladium, platinum, ruthenium, and rhodium. These metals have been found to be particularly useful in combination with the acetylacetonate based structure for selectively hydrogenating halonitro compounds.

The organometallic complexes of the present invention allow the catalytically active metal centers to be highly dispersed on the support. The high dispersion and separation between active metal centers is believed to contribute to the selectivity of the catalyst. The dispersion and/or steric hindrances provide fewer opportunities for partially reduced nitro species to react together to form undesired coupling compounds, such as

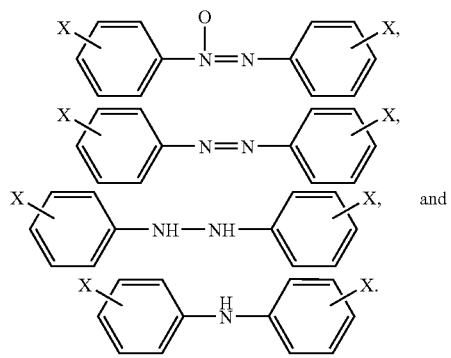

Reducing the formation of undesired coupling compounds results in higher yields of the desired haloamino aromatic compound. It may, in some cases, eliminate the need to distill the haloamino compound.

The bulkiness of the acetylacetonate based ligands provides spacing between the metal centers to facilitate dispersion. The high dispersion and separation between active metal centers is believed to contribute to the selectivity of the catalyst when used for hydrogenation of nitro groups. Because the active centers are spaced apart, there is less opportunity for partially reduced nitro species to react together to form undesired coupling compounds.

The present invention also includes methods for manufacturing the highly selective catalysts of the present invention. In a preferred embodiment, the method includes dispersing a solution or suspension of an organometallic complex on a solid support and reducing the metal atoms to activate the catalyst. The activation step is either performed without oxygen, or where oxygen is present, the catalyst is treated at temperatures below about 100° C. Preparing the catalyst according to steps of the present invention produces a catalyst with higher selectivity for hydrogenating nitro groups.

It is believed that the higher selectivity of the catalysts of the present invention is achieved through one or more of the following features: good dispersion of the metal on the support, separation of catalysts atoms due to the steric hindrances of the organic ligands, separation of catalysts atoms due to bonding with the support, and/or reduced agglomeration during manufacture of the catalyst.

These and other benefits, aspects and features of the present invention will become more fully apparent from the following description and appended claims as set forth hereinafter.

DETAILED DESCRIPTION OF THE PREFERRED EMBODIMENTS

I. Method of Making Catalyst

In general, manufacturing supported catalysts of the present invention includes (i) selecting an organometallic complex that can provide the proper spacing between metal atoms, (ii) selecting a support material, (iii) dispersing the organometallic complex on the support material to form an intermediate supported catalyst, and (iv) activating the intermediate supported catalyst.

A. Organometallic Complexes

The organometallic complexes are compounds that have catalytic metal centers, or that upon further processing of the complex, the metal center can perform a catalytic function. The supported catalysts include a metal center that is coordinated with an acetylacetonate backbone ligand structure. In a preferred embodiment the organometallic complexes have a structure according the following formula:

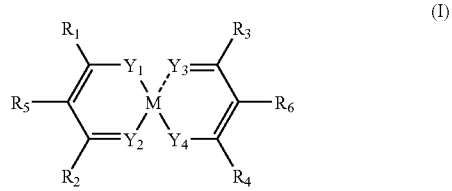

(I)

wherein, $R_1$-$R_6$ comprise, independent of one another, one or more of an R, OR, OC(=O)R, or halide, wherein R stands for an alkyl, an aryl, or a hydrogen;

$Y_1$-$Y_4$ are independently an O, S, N, or P atom; and

M is a metal atom.

The metal atom is selected according to its ability to catalyze hydrogenation of nitro groups of halonitro aromatic compounds. In a preferred embodiment, the metal atom is a palladium, platinum, ruthenium, or rhodium atom. These metals can be complexed with acetylacetonate and its derivatives and are particularly useful for selectively hydrogenating nitro groups.

In a preferred embodiment the metal atoms and the acetylacetonate structure are selected to have a planar structure. If the organometallic complex is planar, the π electrons in the acetylacetonate structure can bond better with the support material.

The organometallic complexes of the present invention allow the catalytic metal centers to be highly dispersed on the support. The bulkiness of the acetylacetonate based ligand structure provides spacing between the metal centers to facilitate dispersion.

Obtaining a desired separation between the metal centers can be accomplished through the selection of $R_1$-$R_6$. In an exemplary embodiment, $R_1$-$R_4$ are $CH_3$ groups and $R_5$ and $R_6$ are H groups (i.e. the metal is complexed with two acetylacetonate ligands). In an alternative embodiment, bulkier radicals are selected for $R_1$-$R_6$ to provide additional spacing. Changing the electronic configuration or steric hindrances of $R_5$ and $R_6$ are particularly effective for modifying the organometallic complex to provide greater dispersion. Suitable radicals for $R_1$-$R_4$ include methyl, benzene, or substituted benzene groups. Suitable bulky radicals for $R_5$ and $R_6$ include methyl, isopropyl, tert-butyl, benzene, or substituted benzene groups. $R_5$ and $R_6$ can be substituted with Cl, Br, or other electron withdrawing groups to modify the ligand electronic configuration.

B. Solid Support

The organometallic complexes are typically supported or formed on a solid support. The support may be organic or inorganic. It may be chemically inert, or it may serve a catalytic function complementary to the catalyst complex.

One useful class of supports includes carbon-based materials, such as carbon black, activated carbon, graphite, fluorinated carbon, and the like. Other supports include polymers and other inorganic solids, metals, and metal alloys.

Another class of support materials includes porous, inorganic materials, such as alumina, silica, titania, kieselguhr, diatomaceous earth, bentonite, clay, zirconia, magnesia, metal oxides, zeolites, and calcium carbonate.

The support may be in a variety of physical forms. It may be porous or nonporous. It may be a three-dimensional structure, such as a powder, granule, tablet, or extrudate. The support may be a two-dimensional structure such as a film, membrane, or coating. It may be a one-dimensional structure such as a narrow fiber. In the case where the support material is porous, it is preferable for the surface area to be at least 1 m²/g, more preferably greater than 20 m²/g.

In a preferred embodiment, the solid support has hydroxyl groups or other functional groups on its surface that would interact with the delocalized electrons of the organometallic complex. This interaction between the support and the organometallic complex facilitates dispersion of the complex on the support and can maintain the dispersed nature of the metal atoms following manufacturing of the catalyst or during use of the catalyst. It is also believed that bonding between the support and the organometallic complex can block access to the metal center on the side of the complex adjacent the support. This feature may be partially responsible for the selectivity of the catalysts in some embodiments of the present invention.

C. Dispersing the Organometallic Complex

The organometallic complex is finely dispersed on the solid support using a solvent. Suitable solvents include any solvent that can dissolve the organometallic complex, including toluene, xylene, chloroethanes, ethers such as diethyl ether, ketones, THF, dichloromethane, benzene, and the like. The solvent, solid support, and organometallic complex are mixed together to disperse the organometallic complex on the support. The mixing can occur in any order. However, the organometallic complex is typically first mixed with the solvent to form a solution or suspension and then mixed with the support.

Dispersing the organometallic complex also includes drying or otherwise removing the solvent from the mixture to form an intermediate catalyst. In one embodiment, the solvent is removed using a rotary evaporator to evaporate the solvent.

The organometallic complex is dispersed on the solid support under conditions suitable to ensure that the complex is not destroyed (i.e. the metal atoms remain complexed with the acetylacetonate derived ligands). For example, the temperature, pressure, and oxidative state of the complex can be controlled to prevent partial or complete removal of the ligands.

In an exemplary embodiment, the step of mixing the solvent, solid support, and organometallic complex is performed at standard temperature and pressure. The drying or solvent removal step is also performed under nondestructive conditions. In a preferred embodiment, the solvent is removed by heating at a temperature less than about 100° C. where oxygen is present, more preferably less than about 90° C. Where oxygen is not present, heating is preferably less than about 150° C. By ensuring that the organometallic complex is not destroyed during dispersion, the metal atoms can be evenly and finely dispersed on the support surface.

The organometallic complex can be loaded on the support within a wide range of loadings. The loading can range from about 0.01% to about 40% by weight of the supported catalyst particles, more preferably in a range of about 0.1% to about 25% by weight.

D. Activating the Intermediate Supported Catalyst

Once the catalyst is dispersed on the solid support material, the catalyst is activating in a reduction step. In a preferred embodiment, the metal atoms of the organometallic complex are reduced using hydrogen. Other suitable reducing agent include alcohols such as methanol and phenol, aldehydes such as formaldehyde, ethylene glycol, hydrocarbons such as methane, ethylene, acetylene, propylene, and other reagents that can be oxidized by the catalyst metals. The reduction step is typically performed at temperatures between about 0° C. and about 160° C.

It is believed that the organic ligand portions of the organometallic complexes at least partially remain complexed to the metal atoms even after activation; however, such binding is not required. By activating the intermediate catalyst after the organometallic complexes have been dispersed on the support surface, at least some of the advantages of using the organometallic complex can be realized.

II. Hydrogenation Of Halonitro Aromatic Compounds

A. Preferred Halonitro Compounds

The catalyst of the present invention can selectively hydrogenate a variety of halonitro aromatic compounds. The aromatic compounds include compounds having structures that follow the Hückels 4n+2 electron rule. For example, suitable aromatic compounds include benzenes, polycyclic hydrocarbons (including partially hydrogenated polycyclic hydrocarbons such as tetralin), biphenyls, cyclopentadienyl anion and cycloheptatrienyl anion, anthraquinones, heteroaromatic substances such as pyridines, pyrroles, azoles, diazines, triazines, furans, thiophenes and oxazoles, condensated aromatic substances such as naphthalene, anthracene, indoles, quinolines, isoquinolines, carbazoles, purines, phthalazines, benzotriazoles, benzofurans, cinnolines, quinazoles, acridines and benzothiophenes. The halogen and nitro groups are preferably bound to carbon atoms of the aromatic nucleus.

The aromatic halonitro compounds also include one or more nitro groups, preferably one or two nitro groups. The aromatic halonitro compounds can also include one or more halogen atoms, preferably one to three halogen atoms. The halogen atoms can be the same or different halogen atoms. Preferred halogens are chlorine and bromine.

The aromatic halonitro compounds may contain further substituents, preferably those without carbon/carbon and carbon/hetero atom multiple bonds.

The aromatic halonitro compounds most preferably correspond to the following formula II:

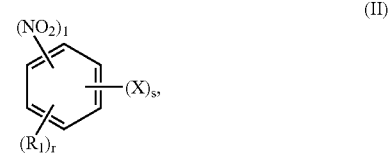

(II)

wherein $R_1$ signifies hydrogen, $C_1$-$C_{12}$-alkyl, $C_1$-$C_{12}$-halogen-alkyl, $C_6$-$C_{16}$-halogen-aryl, $C_3$-$C_6$-halogen-heteroaryl, $C_1$-$C_4$-alkylphenyl, $C_1$-$C_4$-alkoxyphenyl, halogen-$C_1$-$C_4$-alkylphenyl, halogen-$C_1$-$C_4$-alkoxyphenyl, $C_1$-$C_{12}$-hydroxyalkyl, $C_3$-$C_8$-cycloalkyl, $C_3$-$C_8$-cycloalkyl substituted by $C_1$-$C_4$-alkyl, $C_6$-$C_{16}$-aryl, $C_7$-$C_{16}$-aralkyl, $C_3$-$C_6$-heterocycloalkyl, $C_3$-$C_{16}$-heteroaryl, $C_4$-$C_{16}$-heteroaralkyl, $SO_3H$, $SO_2R_2$, $SO_2 N(R_2)_2$, or a group-$Y_1$ $R_2$;

$Y_1$ signifies $NR_2$, oxygen or sulfur;

$R_2$ signifies hydrogen, $C_1$-$C_{12}$-alkyl, $C_1$-$C_{12}$-halogen-alkyl, $C_6$-$C_{16}$-halogen-aryl, $C_3$-$C_{16}$-halogen heteroaryl, $C_1$-$C_4$-alkylphenyl, $C_1$-$C_4$-alkoxyphenyl, halogen-$C_1$-$C_4$-alkylphenyl, halogen-$C_1$-$C_4$-alkoxyphenyl, $C_1$-$C_{12}$-hydroxyalkyl, $C_3$-$C_8$-cycloalkyl, $C_6$-$C_{16}$-aryl, $C_7$-$C_{16}$-aralkyl, $C_3$-$C_6$-hetercycloalkyl, $C_3$-$C_{16}$-heteroaryl, $C_4$-$C_{16}$-heteroaralkyl;

X signifies fluorine, chlorine, bromine or iodine; and r, s, and t, independently of one another, signify a number 1, 2 or 3, whereby r+s+t is less than or equal to six. Preferably, r, s and t, independent of one another, are 1 or 2.

In the above compounds, halogen is a fluorine, chlorine, bromine or iodine. Where there are several halogen substituents, these may be of the same type or mixed (for example Cl and F). Alkyl groups include methyl, ethyl, isopropyl, n-propyl, n-butyl, iso-butyl, sec-butyl, tert-butyl, as well as the various isomeric pentyl, hexyl, heptyl, octyl, nonyl, decyl, undecyl, and dodecyl radicals.

Suitable halogen-alkyl groups includes, for example, fluoromethyl, trifluoromethyl, difluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Suitable alkoxy groups include, for example, methoxy, ethoxy, propoxy, i-propoxy, n-butoxy, i-butoxy, s-butoxy and t-butoxy; preferably methoxy and ethoxy.

Suitable halogen-alkoxy groups include, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy, and trifluoromethoxy.

Suitable cycloalkyl and alkyl-substituted cycloalkyl groups include, for example, cyclopropyl, dimethylcyclopropyl, cyclobutyl, cyclopentyl, methylcyclopentyl, cyclohexyl and cycloheptyl, but preferably cyclopropyl, cyclopentyl, and cyclohexyl.

Suitable alkoxyalkyl groups include, for example, methoxymethyl, ethoxymethyl, propoxymethyl, methoxyethyl, ethoxyethyl, propoxyethyl, methoxypropyl, ethoxypropyl, and propoxypropyl.

Phenyl groups can also be included as part of a substituent such as phenoxy, phenylthio, phenoxycarbonyl, phenylaminocarbonyl, benzyl or benzoyl, and may in general be unsubstituted or substituted by further substituents. These substituents can be in the ortho-, meta-, and/or para-positions. Preferred substitution positions are the ortho- and para-position to the ring attachment site. Preferred substituents are halogen atoms.

Suitable aralkyl groups include, $C_1$-$C_4$-alkyl substituted with phenyl groups, including benzyl, phenethyl, 3-phenylpropyl, α-methylbenzyl, phenbutyl, and α,α-dimethylbenzyl.

Suitable aryl and analogous halogen-aryl groups include, for example, phenyl, tetralinyl, indenyl, naphthyl, azulenyl, and anthracenyl.

Suitable heteroaryl and analogous halogen-heteroaryl groups include, for example, radicals of pyrrole, furan, thiophene, oxazole, thiazole, pyridine, pyrazine, pyrimidine, pyridazine, indole, purine, quinoline, and isoquinoline.

Heterocycloalkyl groups include, for example, radicals of oxirane, oxetane, azetidine, azirine, 1,2-oxathiolane, pyrazoline, pyrrolidine, piperidine, piperazine, morpholine, dioxolane, tetrahydropyran, tetrahydrofuran, and tetrahydrothiophene.

Examples of preferred halonitro aromatic substances are o-, m-, or p-nitrochlorobenzene; o-, m-, or p-nitrobromobenzene; o-, m-, or p-nitrofluorobenzene; 2-chloro-4-nitrotoluene, 2-bromo-4-nitrotoluene, 4-chloro-2-nitrotoluene, 4-bromo-2-nitrotoluene, 6-chloro-2-nitrotoluene, 3-chloro-4-nitroethylbenzene, 2,5-, 2,3-, 2,4-, 3,4-, or 3,5-dichloronitrobenzene, 3,4- or 2,4-dibromonitrobenzene, 4-chloro-6-nitrometaxylene, 3-chloro-4-nitropropylbenzene, 3-chloro-4-nitrobutylbenzene, 1-chloro-8-nitronaphthalene, 1-chloro-2-nitronaphthalene, 1-nitro-5,8-dichloronaphthalene, 3-chloro-4-fluoronitrobenzene, 2-fluoro-4-chloronitrobenzene, 2,4-difluoronitrobenzene, 2,4,5-, 2,3,5-, or 2,4,6-trichloronitrobenzene.

B. Hydrogenation Process

The reactions according to the invention are preferably carried out in the liquid phase, especially with a powdered catalyst, either continuously or discontinuously, as slurry phase hydrogenation or in a bubble column or with a formed catalyst in a fixed bed. The reaction may also be carried out in the gas phase with a powdered catalyst in a fluidized bed or with a formed catalyst in a fixed bed.

2. Solvents

If the halonitro compound to be hydrogenated is liquid at the reaction temperature, hydrogenation may be carried out without solvents, or if the resulting amino compound is liquid under reaction conditions, these may serve as the solvent.

However, it is also possible to add inert solvents. Suitable solvents are for example water, alcohols such as methanol, ethanol, n-propanol, i-propanol, n-butanol, the isomeric butanols and cyclohexanol; ethers, esters and ketone, for example diethylether, methyl-tertiary-butyl-ether, tetrahydrofuran, dioxane, dimethoxyethane, acetic acid ethyl ester, acetic acid butyl ester, butyrolactone, acetone, methyl ethyl ketone, methyl-i-butyl ketone, or cyclohexanone, carboxylic acids such as acetic acid and propionic acid, dipolar-aprotic solvents such as dimethyl formamide, N-methylpyrrolidone, dimethyl acetamide, sulpholane, dimethyl sulphoxide or acetonitrile, apolar solvents such as toluene, xylene, or other aromatics, chlorinated hydrocarbons such as methylene chloride or chloroethanes, $C_3$-$C_7$-alkanes, or cyclohexane.

These solvents may be used alone or as mixtures of at least two solvents. In an especially preferred embodiment of the process according to the invention, the solvents employed are water, methanol, ethanol, iso-propanol, tetrahydrofuran, toluene, or xylene in pure form or as mixtures with the above-mentioned solvents, especially with alcohols and/or $C_1$-$C_4$-carboxylic acids.

2. Reaction Conditions

The process according to the invention may be affected at a pressure between about 1 bar to about 100 bar, preferably at a pressure between about 1 bar to about 40 bar, and most preferably at a pressure between about 1 bar to about 20 bar.

The temperature maintained during the hydrogenation process can be between about 0° C. and about 160° C., preferably between about 20° C. and about 140° C., and most preferably between about 20° C. and about 100° C.

The pH of the reaction mixture can be adjusted to desired value by adding bases or acids.

If solvents are used, the concentration of nitro aromatic substance in the solution is preferably between about 5% and about 50% by weight, most preferably between about 10% and about 30% by weight.

The haloamino aromatic compounds manufactured using the process of the present invention have many uses. For example, some compounds are important chemical intermediates in the manufacture of dyes, pesticides, and pharmaceuticals.

III. EXAMPLES

Example 1

Preparation of Platinum Acetylacetonate on Activate Carbon 6.0 g of activated carbon was soaked in 30 ml methanol for 12 h and then filtered. After filtration the carbon solid was dispersed in 60 ml toluene and a solution of 0.605 g platinum (II) acetylacetonate in 20 ml toluene. The total suspension was continually rotated on a rotary evaporator for 12 h to evaporate the methanol and toluene. The platinum/carbon catalyst was dried in an oven at 80° C. for 6 h and then activated by reducing the catalyst under $H_2$ flow at 100° C. for 4 h. After cooling to room temperature, the catalyst, i.e. platinum acetylacetonate on activated carbon (Pt(acac)/C), was ready for use in a hydrogenation process. The resulting Pt(acac) catalyst had a weight composition of 5% Pt.

Example 2

General Selective Hydrogenation of 2-chloro-nitrobenzene

A typical hydrogenation procedure was conducted as follows: 4.04 g 2-chloro-nitrobenzene catalyst and proper amount of catalyst manufactured in Example 1 was dispersed in 60 ml ethanol. This suspension was placed in a 300 ml stainless steel autoclave equipped with a mechanical stir blade, a pressure gauge, a gas inlet tube attached to a hydrogen source and a cooling circler connected to the temperature controller. The autoclave was purged three times with nitrogen. After stabilizing the temperature at 25° C., the vessel was pressurized to 10.34 bar with hydrogen. The reaction mixture was vigorously stirred and the reaction was stopped when no pressure decrease was observed. The product was analyzed on gas chromatography (Agilent 6890 equipped with a FID detector and Rtx-5 Amine column). The test results for hydrogenation using the platinum acetylacetonate catalyst manufactured according to the present invention are shown in Table 1 below and labeled "Pt(acac)/C".

For comparison purposes, three commercially available catalysts were tested using the same hydrogenation procedure used with the Pt(acac)/C catalyst of the present invention. The three catalysts were obtained from Degussa AG and are characterized by the following: (i) 5% Pt on activated carbon, uniform, reduced, 50% wetted powder; (ii) 5% Pt on activated carbon, eggshell, reduced, 50% wetted powder; (iii) 5% Pt on activated carbon, Bismuth doped, 50% wetted powder. The test results for hydrogenation using commercially available catalyst (i)-(iii) are shown in Table 1 below.

| Catalysts | Reaction Temp. (° C.) | Pressure (bar) | SM/C ratio | Reaction Time (h) | 2-chloro aniline (%) | aniline (%) | Unknown intermediate |
|---|---|---|---|---|---|---|---|
| (i) | 25 | 10.34 | 5,000 | 10.25 | 76.05 | 15.61 | 8.34 |
| (ii) | 25 | 10.34 | 5,000 | 10.25 | 80.82 | 12.09 | 7.09 |
| (iii) | 25 | 10.34 | 5,000 | 20.5 | 90.73 | 0.47 | 8.80 |
| Pt(acac)$_2$/C | 25 | 10.34 | 5,000 | 13.5 | 97.1 | 0.23 | 2.67 |

As shown in the foregoing test runs, hydrogenation of 2-chloro-nitrobenzene using the catalyst of the present invention is highly selective for 2-chloro aniline. The catalyst of the present invention produced only 0.23% of aniline and only 2.67% of other unknown intermediates. In some cases, this high selectivity using the catalyst and methods of the present invention is sufficient to allow the product to be used without distillation, thereby significantly reducing the cost of manufacturing the haloamine.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A process for manufacturing a catalyst for hydrogenating nitro groups, comprising:
    dispersing an organometallic complex on a solid support to form an intermediate supported catalyst, wherein the organometallic complex corresponds to formula I

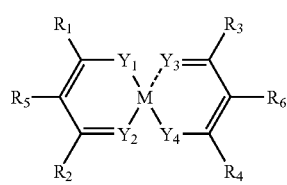

(I)

wherein,
    $R_1$-$R_6$ comprise, independent of one another, one or more of an R, OR, OC(=O)R, or halide, wherein R stands for an alkyl, an aryl, or a hydrogen;
    $Y_1$-$Y_4$ are independently an O or an S atom; and
    M is a metal atom.
    activating the intermediate supported catalyst by reducing the metal atoms; and
    wherein prior to and during activation, the organometallic complexes are not exposed to oxygen at a temperature greater than about 100° C.

2. A process as in claim 1, wherein during use and prior to use, the catalyst is not exposed to oxygen at a temperature greater than about 100° C.

3. A method as in claim 1, wherein the catalyst is dispersed on the support using a solvent.

4. A process as in claim 1, wherein M is selected from the group consisting of platinum group metals.

5. A process as in claim 1, wherein M is selected from the group consisting of palladium, platinum, ruthenium, rhodium, and combinations thereof.

6. A process as in claim 1, wherein the solid support comprises hydroxyl groups on the surface thereof that bond to at least a portion of the organic ligands of the organometallic complex.

7. A process as in claim 6, wherein the solid support comprises carbon.

8. A process as in claim 1, wherein each of $R_1$-$R_4$ is a $CH_3$ group and $R_5$ and $R_6$ are each a hydrogen.

9. A process as in claim 1, wherein $R_1$-$R_4$ are independently a methyl, benzene, or substituted benzene group.

10. A process as in claim 1, wherein $R_1$-$R_4$ each comprise at least one carbon atom.

11. A process as in claim 1, wherein $R_5$ and $R_6$ are independently a hydrogen, methyl, isopropyl, tert-butyl, benzene, substituted benzene, Cl, or Br group.

12. A supported catalyst manufactured according to the process of claim 1.

13. A process for manufacturing an haloamino aromatic compound comprising hydrogenating at least one nitro group of a halonitro aromatic compound in the presence of the catalyst of claim 12.

14. A process as in claim 13, wherein the halonitro aromatic compound has the formula

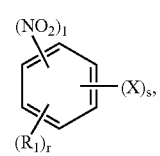

(II)

wherein for the halonitro aromatic compound
    $R_1$ signifies hydrogen, $C_1$-$C_{12}$-alkyl, $C_1$-$C_{12}$-halogenalkyl, $C_6$-$C_{16}$-halogen-aryl, $C_3$-$C_6$-halogen-heteroaryl, $C_1$-$C_4$-alkylphenyl, $C_1$-$C_4$-alkoxyphenyl, halogen-$C_1$-$C_4$-alkylphenyl, halogen-$C_1$-$C_4$-alkoxyphenyl, $C_1$-$C_{12}$-hydroxyalkyl, $C_3$-$C_8$-cycloalkyl, $C_3$-$C_8$-cycloalkyl substituted by $C_1$-$C_4$-alkyl, $C_6$-$C_{16}$-aryl, $C_7$-$C_{16}$-aralkyl, $C_3$-$C_6$-heterocycloalkyl, $C_3$-$C_{16}$-heteroaryl, $C_4$-$C_{16}$-heteroaralkyl, $SO_3H$, $SO_2R_2$, $SO_2N(R_2)_2$, or a group-$Y_1R_2$;

$Y_1$ signifies $NR_2$, oxygen or sulfur;

$R_2$ signifies hydrogen, $C_1$-$C_{12}$-alkyl, $C_1$-$C_{12}$-halogen-alkyl, $C_6$-$C_{16}$-halogen-aryl, $C_3$-$C_{16}$-halogen heteroaryl, $C_1$-$C_4$-alkylphenyl, $C_1$-$C_4$-alkoxyphenyl, halogen-$C_1$-$C_4$-alkylphenyl, halogen-$C_1$-$C_4$-alkoxyphenyl, $C_1$-$C_{12}$-hydroxyalkyl, $C_3$-$C_8$-cycloalkyl, $C_6C_{16}$-aryl, $C_7$-$C_{16}$-aralkyl, $C_3$-$C_6$-hetercycloalkyl, $C_3$-$C_{16}$-heteroaryl, or $C_4$-$C_{16}$-heteroaralkyl;

X signifies fluorine, chlorine, bromine, or iodine; and r,s, and t, independent of one another, signify a number 1, 2, or 3, whereby r+s+t is less than or equal to six.

15. A process for manufacturing an amino aromatic compound, comprising:

hydrogenating at least one nitro group of a nitro aromatic compound in the presence of a catalyst, the catalyst comprising a molecule with a structure according to formula (I)

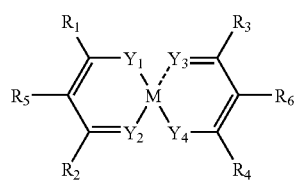

(I)

wherein, $R_1$-$R_6$ comprise, independent of one another, one or more of an R, OR, OC(=O)R, or halide, wherein R stands for an alkyl, an aryl, or a hydrogen;

$Y_1$-$Y_4$ are independently an O or an S atom; and

M is a metal atom.

16. A process as in claim 15, wherein M is selected from the group consisting of palladium, platinum, ruthenium, and rhodium.

17. A process as in claim 15, wherein each of $R_1$-$R_4$ is a $CH_3$ group.

18. A process as in claim 17, wherein each of $R_5$ and $R_6$ is an H group.

19. A process as in claim 15, wherein the catalyst is supported on a solid support.

20. A process as in claim 15, wherein the solid support comprises hydroxyl groups on the surface thereof.

21. A process as in claim 15, wherein the halonitro aromatic compound has the formula:

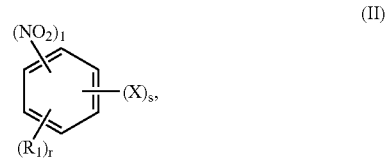

(II)

wherein, for the halonitro aromatic compound $R_1$ signifies hydrogen, $C_1$-$C_{12}$-alkyl, $C_1$-$C_{12}$-halogen-alkyl, $C_6$-$C_{16}$-halogen-aryl, $C_3$-$C_6$-halogen-heteroaryl, $C_1$-$C_4$-alkylphenyl, $C_1$-$C_4$-alkoxyphenyl, halogen-$C_1$-$C_4$-alkylphenyl, halogen-$C_1$-$C_4$-alkoxyphenyl, $C_1$-$C_{12}$-hydroxyalkyl, $C_3$-$C_8$-cycloalkyl, $C_3$-$C_8$-cycloalkyl substituted by $C_1$-$C_4$-alkyl, $C_6$-$C_{16}$-aryl, $C_7$-$C_{16}$-aralkyl, $C_3$-$C_6$-heterocycloalkyl, $C_3$-$C_{16}$-heteroaryl, $C_4$-$C_{16}$-heteroaralkyl, $SO_3H$, $SO_2R_2$, $SO_2N(R_2)_2$, or a group-$Y_1R_2$;

$Y_1$ signifies $NR_2$, oxygen, or sulfur;

$R_2$ signifies hydrogen, $C_1$-$C_{12}$-alkyl, $C_1$-$C_{12}$-halogen-alkyl, $C_6$-$C_{16}$-halogen-aryl, $C_3$-$C_{16}$-halogen heteroaryl, $C_1$-$C_4$-alkylphenyl, $C_1$-$C_4$-alkoxyphenyl, halogen-$C_1$-$C_4$-alkylphenyl, halogen-$C_1$-$C_4$-alkoxyphenyl, $C_1$-$C_{12}$-hydroxyalkyl, $C_3$-$C_8$-cycloalkyl, $C_6$-$C_{16}$-aryl, $C_7$-$C_{16}$-aralkyl, $C_3$-$C_6$-hetercycloalkyl, $C_3$-$C_{16}$-heteroaryl, $C_4$-$C_{16}$-heteroaralkyl;

X signifies fluorine, chlorine, bromine or iodine; and r,s, and t, independently of one another, signify a number 1, 2 or 3, whereby r+s+t is less than or equal to six.

* * * * *